United States Patent [19]

Knöfel et al.

[11] Patent Number: 5,648,519
[45] Date of Patent: Jul. 15, 1997

[54] FRACTIONATION AND PURIFICATION OF AROMATIC POLYAMINE MIXTURES AND THE USE THEREOF

[75] Inventors: Hartmut Knöfel, Odenthal; Michael Brockelt, Leverkusen, both of Germany

[73] Assignee: Bayer Aktiengesesellschaft, Leverkusen, Germany

[21] Appl. No.: 623,235

[22] Filed: Mar. 28, 1996

[30] Foreign Application Priority Data

Apr. 7, 1995 [DE] Germany ............... 195 13 147.9

[51] Int. Cl.[6] .................................................. C07C 209/86
[52] U.S. Cl. ................... 560/347; 564/315; 564/331; 564/332; 564/333; 564/334; 564/437; 564/450; 564/451
[58] Field of Search .................... 564/315, 331, 564/332, 333, 334, 437, 450, 451; 560/347

[56] References Cited

U.S. PATENT DOCUMENTS

| | | | |
|---|---|---|---|
| 4,087,459 | 5/1978 | Knöfel et al. | 564/331 |
| 4,914,236 | 4/1990 | Knöfel et al. | 564/334 |
| 4,924,028 | 5/1990 | Knofel et al. | 564/331 |
| 5,196,591 | 3/1993 | Knöfel et al. | 564/331 |
| 5,359,141 | 10/1994 | Knofel et al. | 564/331 |

FOREIGN PATENT DOCUMENTS

| | | |
|---|---|---|
| 2238319 | 2/1973 | Germany . |
| 1170619 | 11/1969 | United Kingdom . |

OTHER PUBLICATIONS

H. Becker et al "Organikum" 1976 Veb Deutscher Verlag Der Wissenschaften, Berlin XP002005624, pp. 74–82.

*Primary Examiner*—Richard L. Raymond
*Attorney, Agent, or Firm*—Joseph C. Gil

[57] ABSTRACT

The invention relates to a process for the fractionation and purification of aromatic polyamine mixtures and to the use thereof.

10 Claims, 4 Drawing Sheets

FRACTIONATION AND PURIFICATION OF AROMATIC POLYAMINE MIXTURES AND THE USE THEREOF

BACKGROUND OF THE INVENTION

The present invention relates to a process for the fractionation and purification of mixtures of aromatic polyamines and to the use thereof.

The preparation of aromatic polyamines and mixtures of aromatic polyamines, especially of the diphenylmethane series, is described in numerous patent applications and patents, as is the use of these products. Of outstanding importance here is the use of these products as raw materials for the preparation of isocyanates, normally by reaction of the polyamine mixtures with phosgene using the generally conventionally and known methods.

In many cases, however, the resulting isocyanates or isocyanate mixtures are not obtained in the form and with the composition that are preferable for further use at the isocyanate stage, but must first be converted to the usable form by working-up and separation processes which are sometimes expensive. Suitable polyamine precursors which can be converted more cheaply to the forms usable for isocyanates are in many cases difficult or impossible to obtain in terms of process engineering or the economics of their preparation are unattractive.

An example is the preparation of the 4,4'-diisocyanatodiphenylmethane important for the manufacture of high-quality polyurethane materials, whose amine precursor can normally be obtained from aniline and formaldehyde only together with isomers, especially the 2,4'-isomer, and higher-functional polyamines. Although these constituents are the basis for isocyanates which are also desirable, separation of the crude isocyanates into the isocyanates or isocyanate mixtures suitable for further use is not easy.

The normal procedure is first to separate some of the dinuclear compounds from the rest. The 4,4'-diisocyanatodiphenylmethane is then separated from the other isomers in the dinuclear fraction in a second distillation step requiring many separation stages.

In more recent times the 2,4'-isomer in enriched form has itself become increasingly important as a polyurethane raw material, but considerable distillation costs are involved in enriching it relative to the 4,4'-isomer and separating it from the 2,2'-isomer which may be present.

Isomer separation processes or enrichment processes within the fraction of the higher-nuclear homologues or higher-functional constituents of the amines, or of the isocyanates of the diphenylmethane series, are practically unknown.

There is also increasing interest in 4,4'-diaminodiphenylmethane as a raw material for di(4-isocyanatocyclohexyl)methane, the ring-hydrogenated form of 4,4'-diisocyanatodiphenylmethane, it being very expensive to prepare suitable mixtures of aromatic polyamines for the hydrogenation stage with the highest possible content of 4,4'-diaminodiphenylmethane and at the same time the lowest possible proportion of 2,4'-diaminodiphenylmethane.

It is known that amines can be separated in certain cases by partial conversion to their salts, utilizing inter alia the different basic strengths. This normally applies to monoamines with very different basic strengths.

Again for mixtures of aromatic polyamines, especially of the diphenylmethane series, such disproportionation effects have already been described in two-phase systems (German Auslegeschriften 2,238,319 and 2,528,694). Due to the numerous components present in such a mixture whose amino groups hardly differ in type—practically all are arylamino groups—the effects are not sufficiently great and pronounced to be of interest for direct use with simple agents.

The object of the present invention was to provide a process which made it possible to easily fractionate and purify mixtures of aromatic polyamines to give isomers in pure form or in enriched form.

DESCRIPTION OF THE INVENTION

The above could be achieved by the process according to the invention, which attains a surprisingly high separation efficiency in the fractionation of mixtures of aromatic polyamines, especially of the diphenylmethane series, and whose effect well exceeds the known effects of the state of the art.

Other polyamine mixtures of different composition are obtained in the fractionation according to the invention of mixtures of aromatic polyamines. These derived polyamine mixtures may be ones which can only be obtained at very great cost by known synthetic routes. They may also be polyamine mixtures which are more suitable for a simplified preparation of isocyanates than the known polyamine mixtures which are technically easy to prepare, e.g. by anticipating by appropriate enrichments of isomers at the amine stage, isomer separations which are difficult to carry out at the isocyanate stage. By being impossible to prepare according to the state of the art, such mixtures can also be completely novel polyamine mixtures, which lead to completely novel isocyanates.

On the other hand, the process according to the invention can be utilized for obtaining product fractions corresponding to the standard or to the starting polyamines from any desired polyamine mixtures, i.e. including those recovered which differ from the original polyamines or isocyanates used due to contamination or non-statistical (i.e. selective) losses of individual components in the recovery.

Finally, the process according to the invention can be utilized for co-fractionating by-products and intermediates arising from the synthesis and not desired in the end product, depleting them in one product fraction and correspondingly enriching them in another, and optionally removing them in a separate fraction.

The present invention relates to a broadly applicable process which makes it possible to achieve the object of fractionating and purifying mixtures of aromatic diamines and polyamines, especially of the diphenylmethane series.

The invention provides a process for the fractionation and purification of mixtures of aromatic polyamines, in particular of polyamine mixtures of the diphenylmethane series, which is characterized in that a) the starting polyamine mixture (A) is distributed, by means of an extraction stage (3) operating according to the countercurrent principle, in a two-phase system, consisting of (i) a hydrophobic solvent phase (B), which consists substantially of hydrophobic solvent and optionally of an aromatic auxiliary amine, which amine is virtually insoluble in water and at normal pressure has a boiling point at least 20° C. below the boiling point of the lowest boiling component of the starting mixture and at least 20° C. above the boiling point of the solvent, and optionally of polyamines, and (ii) an aqueous phase (C), consisting substantially of water, a strong acid and auxiliary amine present at least partly in the form of salt, and optionally polyamines present at least partly in the form of salt, with thorough mixing of the phases, by introducing the starting polyamine mixture into the extraction stage (3) via the organic phase (B), by at least partly separating the organic phase (D) leaving this extraction stage, optionally after passing through a washing stage (7.0), in a multiple-stage distillation (7.1), (7.2) into a first fraction (E) which is reused in the extraction stage (3) and consists substantially of hydrophobic solvent and optionally auxiliary amine, into a second fraction (F), consisting substantially of auxiliary amine and optionally of hydrophobic solvent, and a distillation residue (G), consisting substantially of a first polyamine fraction, and by passing the aqueous phase (H) leaving the extraction stage (3), b) optionally at least partly via an interposed extraction stage (4), c) into an extraction stage (5), wherein the aqueous phase is extracted according to the principle of countercurrent extraction, using a solvent phase (J) consisting of hydrophobic solvent and auxiliary amine, and the aqueous phase (K) depleted of polyamine results, and d) by at least partly separating the organic phase (L) obtained in the extraction stage (5), optionally after passing through a washing stage (8.0), in a multiple-stage distillation (8.1), (8.2) into a first fraction (M), consisting substantially of hydrophobic solvent and optionally small proportions of auxiliary amine, and into a second fraction (N) consisting substantially of auxiliary amine and optionally small proportions of hydrophobic solvent and a distillation residue (O), consisting substantially of a second polyamine fraction, and e) by passing at least partly the aqueous phase (K) obtained in the extraction stage (5), f) optionally via an interposed distillation stage (9)

g) into an extraction stage (6) and by extracting it in countercurrent using an organic phase (P), consisting substantially of hydrophobic solvent and optionally of at most sufficient auxiliary amine to obtain in (6) an aqueous phase (Q) depleted of arylamine as compared with the aqueous phase (K) introduced, which phase (Q), h) optionally at least partly via an interposed distillation stage (9)

i) is combined with the residue of (Q) optionally present and is reused as stream (C), by passing stream (C)

j) optionally at least partly via an extraction stage (2) serially connected in front k) optionally after addition of auxiliary amine and/or water, to the extraction stage (3) and l) by passing the organic phase (R) obtained in the extraction stage (6), optionally after addition of another organic phase, consisting substantially of auxiliary amine and diverted from stream (S), as extracting agent (J) to the extraction stage (5).

The numbers and capital letters above and in the description which follows refer to elements and streams in the drawings.

The process is preferably carried out in such a way that the aqueous phase (H) obtained in the extraction stage (3) is extracted at least partly in an extraction stage (4) serially connected behind and operating according to the countercurrent principle, using as extracting agent an organic phase (T) which consists, in addition to hydrophobic solvent, of auxiliary amine and optionally of polyamine, the latter preferably having the composition of the second partial product (O) and preferably introduced as a partial quantity of the stream (L); the resulting organic phase (U) in the processing stage (4) is passed to the stream (B) and therewith to the extraction stage (3) and the resulting aqueous phase (V) is passed to the extraction stage (5).

The process according to the invention is particularly preferably carried out in such a way that a partial quantity (D") of the organic phase (D) leaving the extraction stage (3) is separated off and is extracted in a preferably multiple-stage extraction stage (2) positioned in front, using preferably the entire stream (C) in countercurrent, optionally with the addition of auxiliary amine, and the partial stream (D") is calculated so that as extensive a transition as possible of the polyamine contained in (D") into the aqueous phase leaving the extraction stage (2) takes place, the said aqueous phase, optionally after addition of water from stream (Y) and/or auxiliary amine and/or further aqueous phase from stream (C), is passed to the extraction stage (3), the organic phase (Z) obtained in (2) and consisting substantially of hydrophobic solvent and optionally auxiliary amine is likewise passed to the extraction stage (3) and as a constituent of the organic phase (B) is used as solvent for the starting polyamine (A).

The reused stream (C) exhibits a higher degree of protonation than that of the aqueous phase (K) leaving the penultimate extraction stage (4), optionally by up to 100%.

A further improved and therefore preferred embodiment of the process according to the invention is achieved by freeing at least partly the aqueous phase (K) leaving the extraction stage (5) prior to reuse thereof and/or at least partly the aqueous phase (Q) leaving the extraction stage (6) prior to reuse thereof, by means of distillation (9), from a portion (X) of the water contained therein, by optionally using the latter for washing (7.0) the portion of the organic phase (D) leaving the extraction stage (3) and led away for working up by distillation (7.1), (7.2) and/or for washing (8.0) the portion of the organic phase (L) leaving the extraction stage (5) and led away for working up by distillation (8.1), (8.2), in order to remove traces of acid, by returning the water (Y) obtained here into the aqueous phase at a suitable place, by combining the resulting concentrated aqueous phase with the optionally remaining residues of (K) and (Q) and returning it for reuse as stream (C).

More specifically, the present invention, in its broadest embodiment, is directed to a process for the fractionation and purification of aromatic polyamine mixtures, in particular of polyamine mixtures of the diphenylmethane series, comprising:

a) mixing the polyamine starting mixture (A) in a first extraction stage (3) with a two-phase system comprising (i) a hydrophobic solvent phase (B) which consists essentially of hydrophobic solvent and optionally an aromatic auxiliary amine which is substantially insoluble in water and exhibits at normal pressure a boiling point which is at least 20° C. below the boiling point of the lowest-boiling component of the starting mixture and at least 20° C. above the boiling point of the solvent, and optionally polyamine, and (ii) an aqueous phase (C) consisting essentially of water, a strong acid and auxiliary amine present at least in part in the salt form, and optionally polyamines present at least in part in the salt form, with said first extraction stage (3) operating on the countercurrent principle, and wherein said polyamine starting mixture (A) is introduced into said first extraction stage with hydrophobic solvent phase (B), with a first aqueous phase (H) and a first organic phase (D) exiting said first extraction stage (3), b) distilling said first organic phase (D) in a first multi-stage distillation (7.1), (7.2) into
  i) a first fraction (E) consisting essentially of hydrophobic solvent and optionally auxiliary amine,
  ii) a second fraction (F) consisting essentially of auxiliary amine and optionally hydrophobic solvent, and
  iii) a distillation residue (G) consisting essentially of a first polyamine fraction, c) extracting said first aqueous phase (H) in a second extraction stage (5) with a solvent phase (J) consisting essentially of hydrophobic solvent and auxiliary amine, said second extraction stage (5) operating on the countercurrent principle, with i) a second aqueous phase (K), said second aqueous phase being reduced in polyamine content and ii) a second organic phase (L) exiting said second extraction stage (5), d) separating at least a portion of said second organic phase (L) in a second multi-stage a first fraction (8.1), (8.2) into
  i) a first fraction (M) consisting essentially of hydrophobic solvent and optionally proportions of auxiliary amine,
  ii) a second fraction (N) consisting essentially of auxiliary amine and optionally proportions of hydrophobic solvent, and
  iii) a distillation residue (O) consisting essentially of a second polyamine fraction, e) extracting at least a portion of said second aqueous phase (K) in a third extraction stage (6) with an organic phase (P) consisting essentially of hydrophobic solvent and optionally auxiliary amine, said third extraction stage (6) operating on the countercurrent principle, with i) a third aqueous phase (Q), said third aqueous phase being reduced in amine content and ii) a third organic phase (R) exiting said third extraction stage (6), f) recycling said third aqueous phase (Q) as at least a portion of stream (C), and g) recycling said third organic phase (R) to said second extraction stage (5) as at least a portion of solvent phase (J).

The auxiliary amine used is preferably aniline and the polyamine mixture of the diphenylmethane series used is preferably a polyamine mixture obtained during the acid-catalyzed aniline/formaldehyde condensation.

The polyamine mixtures thus treated, that is, the fractions produced by the process according to the invention, are used for the preparation of the corresponding aromatic polyisocyanate mixtures and for the production of polyurethane plastics. The fractions produced by the process according to the invention can moreover be used for the preparation of corresponding ring-hydrogenated polyamines or as cross-linking agents and as curing agents for epoxides. The corresponding polyisocyanates prepared from the fractionated polyamine mixtures are used preferably for the production of PU foamed plastics.

Starting mixtures are, for example, technical arylamine mixtures, obtained during the preparation from the starting compounds or during recovery.

The process according to the invention is particularly suitable for the fractionation and purification of, for example, the following starting arylamine mixtures 1. polyamine mixtures of the diphenylmethane series, formed during the condensation and acid-catalyzed rearrangement of aniline with formaldehyde,
2. polyamine mixtures of the diphenylmethane series, obtained during the acid-catalyzed condensation of substituted anilines with formaldehyde,
3. polyamine mixtures of the diphenylmethane series, obtained during the mixed condensation of substituted anilines with one another and/or with aniline together with formaldehyde,
4. polyamine mixtures of the diphenylmethane series, obtained during the condensation, also during the mixed condensation of substituted anilines and/or aniline together with aldehydes and/or ketones,
5. polyamine mixtures of the diphenylmethane series, formed during the nitration and subsequent reduction of di- and/or polyarylmethanes and/or substituted di- and/or polyarylmethanes; the polyarylmethanes referred to here are in particular the benzyl homologues of diphenylmethane,
6. polyamine mixtures of the diphenylmethane series, formed during the condensation of monoarylmonoamines (for example, aniline, substituted anilines) and/or monoaryl-diamines (phenylene-diamines, substituted phenylene-diamines) with aldehydes, ketones, in particular formaldehyde, and acid-catalyzed rearrangement and
7. polyamine mixtures of the triphenylmethane series, formed, for example, during the nitration and subsequent reduction of trimethylmethane, in particular of alkyl-substituted triphenylmethanes, and of its higher nuclear, in particular benzyl, homologues.

The hydrophobic solvents used are inert solvents within the boiling point range of 30° to 280° C., preferably of 80° to 200° C., such as, for example, chlorobenzene, dichlorobenzene, benzene, toluene, ethylbenzene, cumene, xylene, dichloroethane, chloroform and carbon tetrachloride. Preferably xylenes, that is, technical xylene mixtures, in particular o-xylene, toluene, ethylbenzene, cumene and chlorobenzene are used. Preferably those solvents are employed which exhibit a good capacity to dissolve the polyamine mixtures used.

The acids used are water-soluble proton donors having a pKA value of below 2.5, preferably below 1.5. Examples of these are hydrochloric acid, hydrobromic acid, sulfuric acid, trifluoroacetic acid, methanesulphonic acid or phosphoric acid. Preferably hydrochloric acid and methanesulphonic acid are used. The above-mentioned acids can also be used in a mixture with acidic and neutral salts of these acids such as, for example, the corresponding ammonium salts or else the corresponding alkali salts. The above-mentioned acids are not used in the free form, but are present in the circulation system according to the invention in the form of the corresponding ammonium salts of the bases contained in the aqueous circulation system. These are as a rule polyamine mixtures of the type of the starting mixtures and/or the auxiliary amines employed.

As a rule monoarylamines such as, for example, aniline and/or aniline derivatives alkyl-substituted on the ring and/or on the nitrogen atom are used as auxiliary amine. Preferably primary anilines are used; aniline is particularly preferred.

The process according to the invention can be carried out both batchwise and continuously. The continuous mode of operation is the preferred embodiment. In this case all stages in the process are carried out at the inherent pressure of the system and preferably in an inert gas atmosphere (nitrogen).

The process according to the invention can be repeated with each of the fractions of product obtained in order to increase the enrichment effect or corresponding depletion effect.

Figure 1:
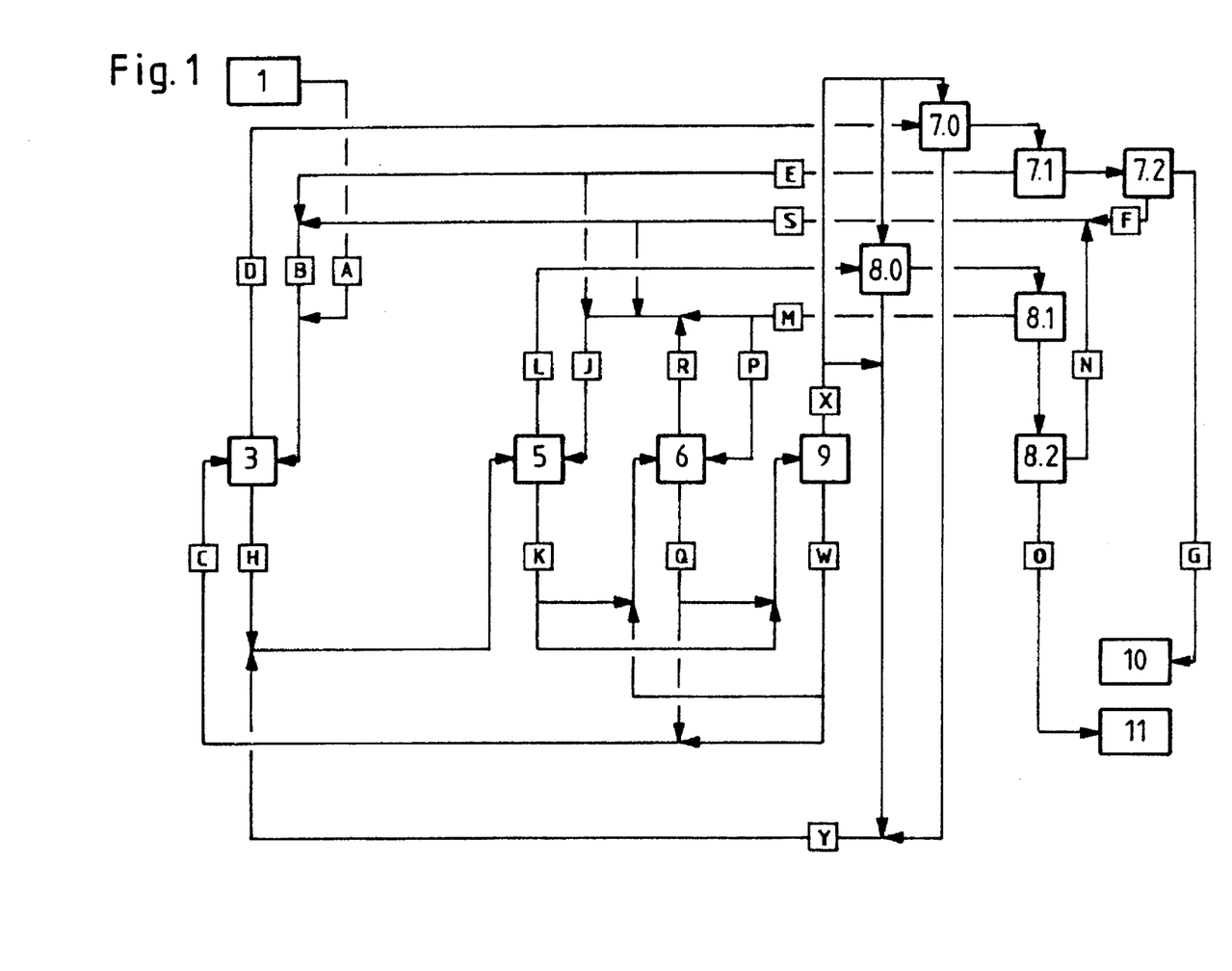
FIGS. 1 through 4 represent flow diagrams for various embodiments of the present invention.
Figure 2:
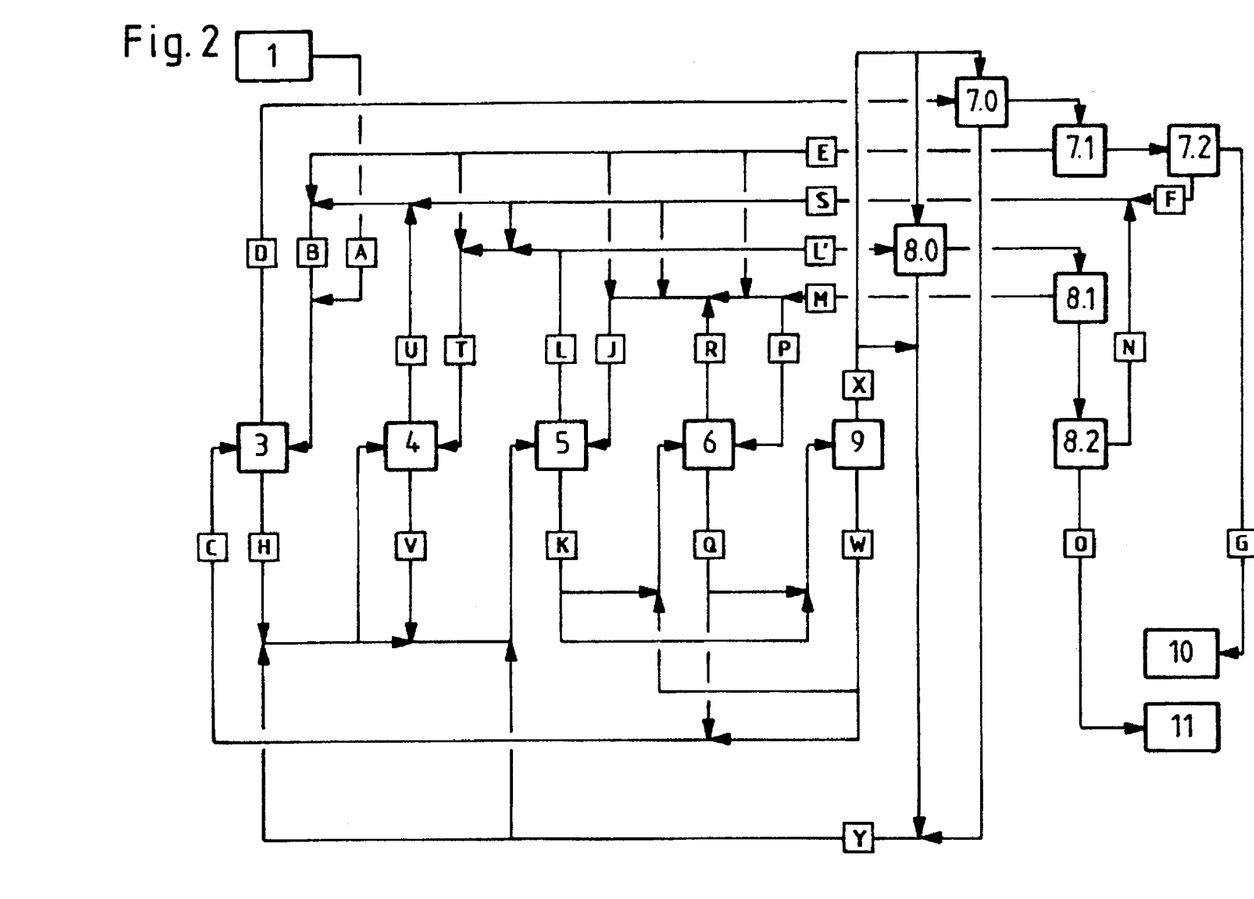
Figure 3:
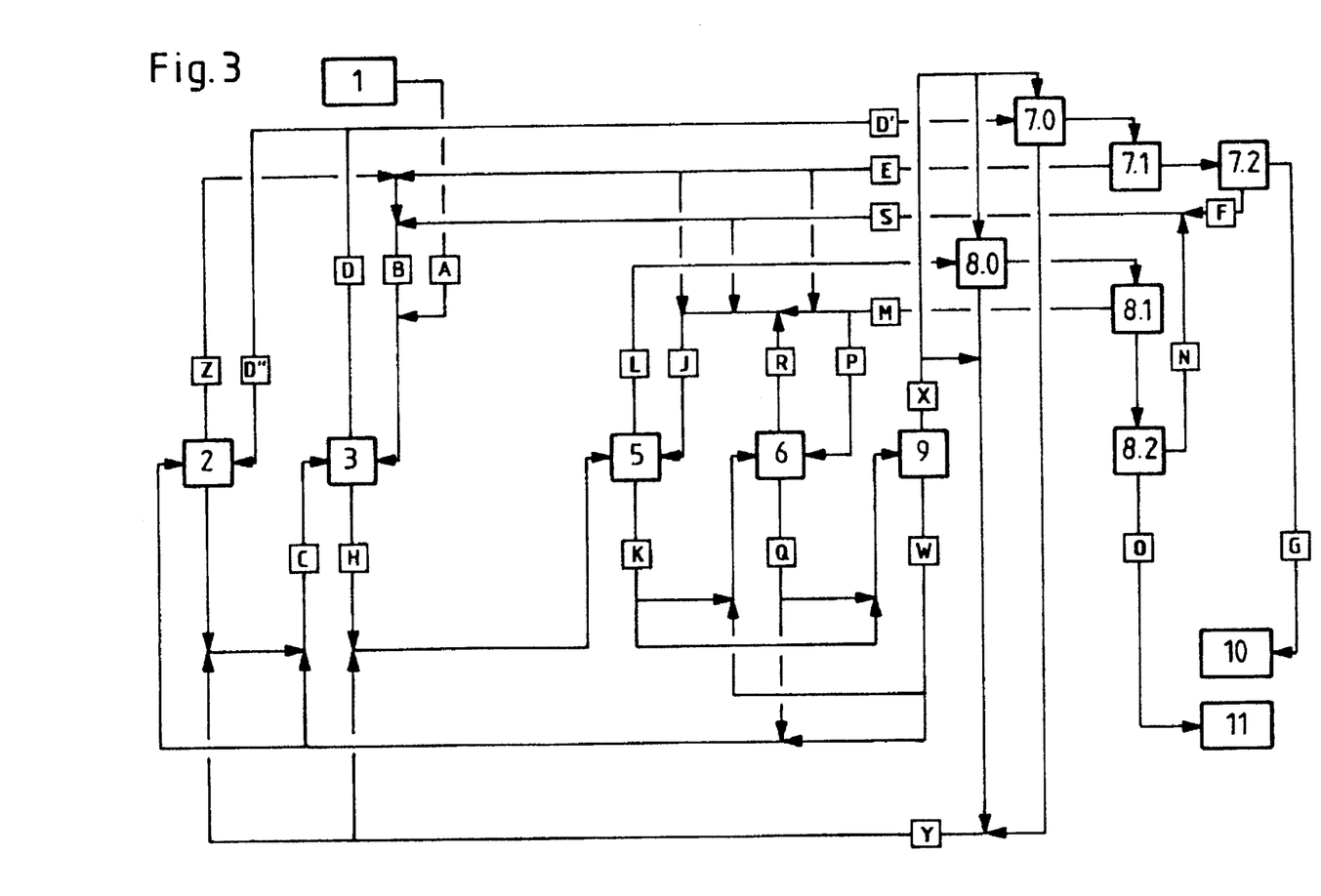
Figure 4:
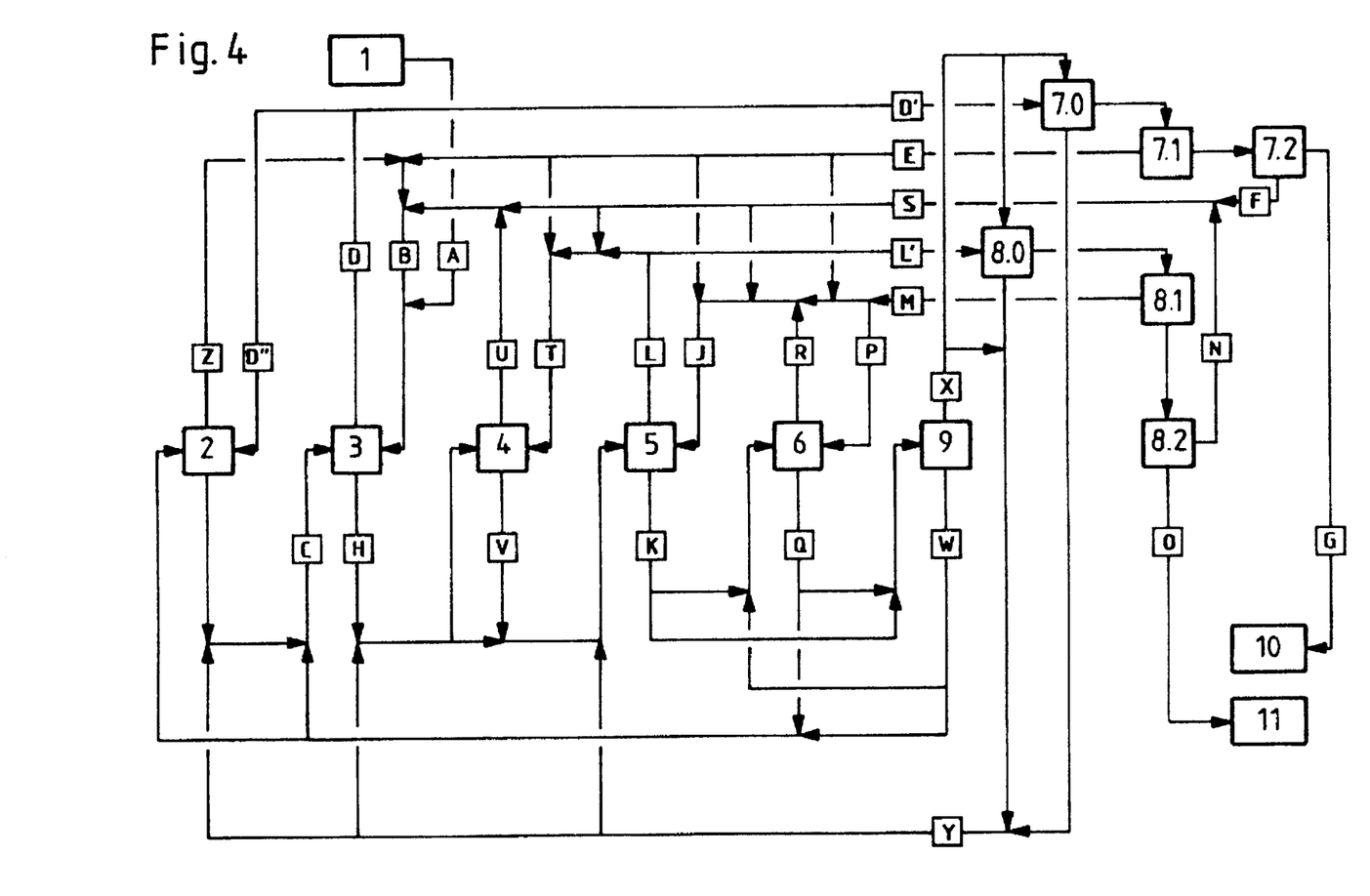

The process according to the invention can be carried out with three (FIG. 1) as well as with four (FIG. 2 and FIG. 3) or with five extraction stages (FIG. 4).

The flow diagrams shown in FIGS. 1 to 4 serve further to illustrate the process according to the invention. The numerals in these Figures indicate the following:

(1) a tank for the starting arylamine mixture
(2) an extraction stage serially connected in front
(3) a first extraction stage
(4) an (interposed) second extraction stage
(5) a (penultimate) third extraction stage
(6) a (final) fourth extraction stage
(7) a working-up stage comprising
   (7.0) a washing stage
   (7.1) a first distillation stage of a multiple-stage distillation
   (7.2) a final distillation stage of a multiple-stage distillation
(8) a further working-up stage comprising
   (8.0) a washing stage
   (8.1) a first distillation stage of a further multiple-stage distillation
   (8.2) a final distillation stage of a further multiple-stage distillation
(9) a water evaporator
(10) a tank for the collection of a product of the process
(11) a tank for the collection of a further product of the process.

The letters A to Z indicate the streams, to which reference is made below and in the Examples.

The extraction stage (2) serially connected in front is generally carried out using a multiple-stage extractor.

The extraction stage (3) in the simplest case involves a mixer-settler unit operating in a single stage, but preferably multiple-stage extraction units are used.

The optionally interposed extraction stage (4) in the simplest case consists of a mixer-settler unit, but here also preferably multiple-stage extraction units are used.

The extraction stages (5) and (6) are generally carried out using multiple-stage extractors.

The working-up stages (7) and (8) serve to separate off the polyamine fractions, which are obtained as distillation residues and are isolated in the tanks (10) and (11) as products (G) and (O) of the process, and to recover as distillates the hydrophobic solvent used and the auxiliary amine employed.

In general the recovery of hydrophobic solvent and auxiliary amine is associated with an extensive, optionally complete, separation of both components and is carried out with the recovery of hydrophobic solvent which is at least to a large extent depleted of auxiliary amine, optionally to a large extent freed from auxiliary amine, in the form of the flows of distillate (E) and (M) on the one hand, and of auxiliary amine which is at least to a large extent depleted of hydrophobic solvent, optionally largely freed from hydrophobic solvent, in the form of the flows of distillate (F) and (N), as a rule combined in the stream (S).

It has proved useful, prior to their distillation, to free the organic phases (D) or (D') and (L) or (L') passed to the distillation stages from adhering traces of acid by extraction with water in washing stages (7.0) and (8.0) positioned in front.

The actual working-up stage (7) generally consists of an at least two-stage multiple-stage distillation, the first stage (7.1) whereof supplies as distillate (E) a hydrophobic solvent freed from polyarylamine as compared with the feed product (D) or D') and applied of auxiliary amine, optionally freed from auxiliary amine, and the final stage (7.2) whereof supplies as distillate (F) an auxiliary amine freed from polyarylamine as compared with (D) or (D') and depleted of hydrophobic solvent, optionally freed from hydrophobic solvent.

In addition the first polyamine fraction of the starting mixture (A) contained in the stream (D) or (D') is obtained in the final distillation stage (7.2) as distillation bottoms (G).

The working-up stage (8) also generally consists of an at least two-stage multiple-stage distillation, the first stage (8.1) whereof supplies as distillate (M) a hydrophobic solvent freed from polyamine as compared with the feed product (L) or (L') and depleted of auxiliary amine, optionally freed from auxiliary amine, and the final stage (8.2) whereof supplies as distillate (N) an auxiliary amine freed from polyarylamine as compared with (L) or (L') and depleted of hydrophobic solvent, optionally freed from hydrophobic solvent.

In the carrying out of the process according to the invention the extensive, optionally complete, separation by distillation of hydrophobic solvent and auxiliary amine is preferred; this applies in particular to the distillate fractions (M) and (E).

The distillation stage (9) involves a device whereby water can be withdrawn by distillation from the aqueous phase of the system or from a partial stream of the aqueous phase.

Such a stage is not in principle necessary for carrying out the process according to the invention, but the embodiments incorporating a water distillation stage (9) are preferred because of the ensuing advantages.

In the aqueous phase containing the acid there is in practice a closed circulation system, so that the stage (9) can in principle be inserted at any position in this circulation system. The positioning of stage (9) subsequent to the extraction stage (6) and, prior to entry to the extraction stage (2) or (3) is the most advantageous and therefore the preferred embodiment.

The quantity of water (X) withdrawn, optionally after it has been divided into partial streams and the-latter have been put to various uses, is returned in the form of the stream (Y) as a whole, or in partial streams, to the system at a suitable place, so that an extended and optionally branched self-contained aqueous circulation system is formed.

This also includes the washing stages (7.0) and/or (8.0). The latter are extraction stages operating according to the countercurrent principle, in a single stage or in multiple stages. In washing stage (7.0) the organic phase (D) or D') is freed from adhering traces of acid by means of a partial stream of (X); in the washing stage (8.0) a similar procedure takes place with the organic phases (L) or (L'), using another partial stream of (X).

The distillate (X) contaminated with hydrophobic solvent and auxiliary amine is most suitable for the washing stages (7.0) and (8.0). The resulting washings as a rule have a very much lower acid concentration than the actual acid circulation has, so that these washings can be recirculated without problems in the form of the stream (Y) or the partial streams thereof, optionally a part of the distillate from (X) can bypass the washing stages and be led to (Y) and employed to regulate a varying water content in the individual extraction stages.

The virtually quantitative recirculation of the acid used renders possible the use of costly acids such as, for example, methanesulphonic acid, which in turn, owing to its low tendency to corrode, permits the use of economical materials in the apparatus of the process according to the invention.

It has proved useful to define the acid content of the aqueous phase, independent of the varying amine content arising in the aqueous phase of a two-phase system, by means of a so-called "molarity". The molarity is defined as the theoretical concentration of 100% protonated amine (that is, an equal number of acid and amine equivalents) in a volume of aqueous phase theoretically diminished by the proportion of non-protonated amine, according to the formula $$\text{"molarity"} = \frac{\text{mol of 100\% protonated amine}}{\text{vol. aqu. phase} - \text{vol. unprotonated amine}}$$

The molarity defined in this way can assume values of up to 6 and is purposively varied within this range according to the—here product-related—problem of separation underlying the respective embodiment.

Within an embodiment of the process according to the invention it may also optionally be advantageous to operate the individual processing stages through which the aqueous phase is passed, in particular the extraction stages (2) to (6), with a varying molarity in the aqueous phase, by withdrawing or adding water to the aqueous phase between the individual stages.

This operating range is in practice restricted towards the upper end on the one hand by the increasing tendency of the amine salts to crystallize with increasing concentration, in particular at high degrees of protonation, and on the other hand by the increasing mutual solubility of the phases with one another, in particular at low degrees of protonation.

The degree of protonation expresses the ratio of acid equivalents to amine equivalents.

This range is restricted towards the lower end for economic reasons, owing to the decreasing acid content and therewith the quantitative decline in separation efficiency, that is, for an excellent qualitative separation efficiency which is free from technical problems, with decreasing molarity an increasingly large volume of aqueous phase is necessary for the separation of a given quantity of amine.

In one variant of the process according to the invention, the feed of the starting polyamine mixture (A) from the storage tank (1) takes place by mixing with the flow (B), formed from the stream (E) from the first distillation stage (7.1), consisting of hydrophobic solvent and optionally auxiliary amine, and optionally a partial stream from (S).

In general the content of arylamine, consisting of starting polyamine and auxiliary amine, present in stream (B) after addition of (A) is from 10 to 80 wt. %, preferably from 15 to 60 wt. %.

The content of starting polyamine in stream (B) after addition of (A) is generally from 5 to 60 wt. %, preferably from 10 to 40 wt. %.

In the extractor (3), the stream (B) charged with (A) is passed through counter to the aqueous phase (C).

In general the stream (C) consists of water, a strong protonic acid, auxiliary amine and optionally polyamine. The acid is present in the form of its water-soluble salt together with auxiliary amine and optionally polyamine. The sum of the amine groups of the auxiliary amine and optionally polyamine is invariably present in (C) in stoichiometric proportion or in excess, referred to the acid.

The degree of protonation in (C) is generally from 40 to 100%; for aniline, which is preferably used as auxiliary amine, it is preferably from 60 to 100%.

The molarity of the stream (C), which is clearly defined and is measured and controlled within narrow limits for the respective embodiment of the process according to the invention, is purposively varied within a wide range according to the—here product-related—problem of separation underlying the respective embodiment.

In general the aqueous phase (C) passed to the extraction stage (3) of the process according to the invention has a molarity of between 0.5 and 4.5. Within the extraction stage (3), which is preferably operated in multiple stages, the stream (B) charged with (A) and the aqueous phase (C) are passed counter to one another with intimate mixing.

During this process a transition of polyarylamine from the organic phase (B) into the aqueous phase takes place as a rule, optionally in exchange for auxiliary amine in the opposite direction.

In the aqueous phase (H) leaving the extraction stage (3) the acid is present as an aqueous solution of its ammonium salts together with polyamine and optionally auxiliary amine, which solution as a rule contains dissolved free polyamine, that is, not bound in the form of a salt, and optionally free auxiliary amine, that is, not bound in the form of a salt.

The starting polyamine (A) introduced together with the organic phase (B) into the extractor (3) is distributed between the aqueous phase (H) leaving the extractor and the organic phase (D) leaving the extractor (3) (quantitative fractionation).

The quantitative distribution of the individual components of the starting polyamine mixture between the resulting aqueous phase (H) and the resulting organic phase (D) takes place with a surprisingly high selectivity under the conditions of the process according to the invention, so that the resulting product fractions are of another composition, greatly differing from that of the starting polyamine mixture (qualitative fractionation).

For example, starting from the preferably used products of aniline formaldehyde condensation, it was found that from a polyamine component present in two or more isomeric forms in the starting mixture, as a rule the ortho-isomeric form(s) is (are) relatively enriched in the organic phase (D) leaving the separator stage (3); for example, 2,4'-diaminodiphenylmethane relative to 4,4'-diaminodiphenylmethane. Conversely, the resulting aqueous phase (H) is relatively depleted of the 2,4'-isomer, whereas the 4,4'-isomer is relatively enriched.

If several "ortho-isomers" are present in the starting polyamine, for example, 2,2'- and 2,4'-diaminodiphenylmethane, then the "ortho-richer" 2,2'-isomer is more highly enriched in the organic phase (D) as compared with the "ortho-poorer" 2,4'-isomer, which latter is for its part relatively enriched as compared with the "even ortho-poorer" 4,4'-isomer.

The enrichment and depletion effect first found in the compounds of the diaminodiphenylmethane series obtained as products of aniline/formaldehyde condensation was associated purely empirically and descriptively with the measure of ortho- and para-substitution. The characterization, derived therefrom, of products of a process as "ortho-rich" or "ortho-poor" is relative and was expressed by the term "degree of ortho-substitution".

In this connection "degree of ortho-substitution" is defined as the proportion of ortho amino group-methylene group bonds of the total number of all amino group bonds. Using this concept, it is possible to identify virtually all separations of isomers in the polyamines prepared in aqueous acid medium from arylamines, including substituted arylamines, and carbonyl compounds.

Surprisingly, the identical enrichment and depletion effect—graded according to degree of ortho-substitution—has now also been found for the well-characterized and analytically identifiable isomeric trinuclear compounds obtained from aniline/formaldehyde condensation. This applies similarly to the separation of the isomers of condensation products of formaldehyde with aniline and diaminoaryl compounds such as phenylenediamine or alkyl-substituted phenylenediamines.

The polyamine mixtures hitherto mentioned, owing to the method of their preparation, have amino groups which are virtually only in the ortho and/or para position to methylene groups. Here, within a group of isomeric compounds, as a rule those having the higher degree of ortho-substitution are enriched in the organic phase (D) during fractionation as compared with the isomers having a lesser degree of ortho-substitution.

Polyamine mixtures, particularly of the diphenylmethane series, including the respective higher nuclear homologues, which are prepared by other processes, for example, by nitration of diphenylmethane or methyldiphenylmethanes and subsequent reduction, possess in addition to amino groups in the ortho and para positions, other amino group-methylene group bonds as well, owing to the method of their preparation. The process according to the invention is equally efficient for these polyamine mixtures. For example, from a mixture of 2- and 4-methyldiphenylmethane it is possible to prepare, by nitration and subsequent reduction, a polyamine mixture which is chiefly an isomeric mixture of During the fractionation of such a mixture by means of the process according to tile invention, the 3,2'-amino isomers are enriched in the organic phase (D) as compared with the 3,4'-amino isomers.

The criterion "ortho-rich" and "ortho-poor" or the degree of ortho-substitution no longer identifies all isomers in these polymer mixtures and is therefore to be used in the general sense, while instead of the terms "in the ortho position" or "in the para position" a classification is made of the isomers into those having a smaller (=ortho) and those having a larger (=para) spatial distance of the—as a rule positioned on different six-membered rings—amino groups to the methylene bridges or of the amino groups to one another.

Another class of aromatic polyamine mixtures which can be fractionated very efficiently by means of the process according to the invention is represented by the polyamines of triphenylmethane and the higher nuclear homologues thereof, preferably benzyl homologues, which are prepared, for example, by nitration and subsequent reduction of the corresponding hydrocarbon mixtures.

In the fractionation of technical polyamines of the classes of substances finally mentioned above I. mixed condensation products of mono- and diaminoaryl compounds with formaldehyde or general carbonyl compounds, II. polyamine mixtures obtained from tile process by nitration and subsequent reduction of diphenylmethane and preferably substituted, in particular alkyl-substituted, diphenylmethanes and the respective homologues and III. polyamine mixtures obtained from the process by nitration and subsequent reduction of triphenylmethane and preferably substituted, in particular alkyl-substituted, triphenylmethanes and the respective higher nuclear benzyl homologues a further surprising selectivity was found in addition to the separation of pure isomers.

Polyamine mixtures of the above-mentioned classes of substances I to III contain or may contain components wherein at least one aryl ring per molecule contains more than one, as a rule two, amino groups. These components can be the preferred constituents of the polyamine mixture, without their having to be the main product quantitatively produced by the process.

In order better to characterize these components, the term "degree of amino substitution" is used, which characterizes primarily the number of amino groups of a component in proportion to the number of aryl rings. For aniline and its condensation products with formaldehyde, this expression is invariably 1.0 and for phenylenediamine and its condensation products is invariably 2.0. For pure mixed condensates, the value of 1.5 is obtained for the diphenylmethane isomers and values of between >1.0 and <2.0 are obtained for the higher nuclear homologues. When the term "degree of amino substitution" is used statistically to characterize the polyamine mixtures, values of between 1.0 and 2.0 again result.

During the fractionation of polyamine mixtures having components with a degree of amino substitution of >1.0, it has now been found that the components having a higher degree of amino substitution are relatively enriched in the aqueous phase (H) obtained in the actual separator stage, in fact the more so, the greater the degree of amino substitution.

Regardless of this, the separation according to degree of ortho substitution is also efficient here. Consequently the process according to the invention also opens up for these classes of substances new ways of dissociating the form in which the raw materials are prepared (amine stage) and the form in which the end products are used (isocyanate stage) by fractionation and/or enrichment at the amine stage and separate further processing of the fractions, so that a separate optimization of the two stages is now rendered easier for the recovery of completely new isocyanate mixtures or becomes possible for the first time where hitherto suitable processes and methods have been lacking or impracticable.

These "achievements" are supplemented by a further measure of selectivity, which has been found in the course of fractionating technical polyamine mixtures, in particular those having higher nuclear homologues, and which relates to the "nuclearity" of the polyamine mixtures. The term "nuclearity" expresses primarily the number of aryl units of a component of a mixture of aromatic polyamines. In a wider sense, the term number of rings is used in order to express statistically a number of rings for the overall mixture in the case of a polyamine mixture consisting of numerous components individually having a precise number of rings.

Particularly surprisingly, it has now been found that during the fractionation of polyamine mixtures having higher nuclear components, in particular during the fractionation of technical mixtures of aniline/formaldehyde condensates, the higher nuclear components in the organic phase leaving the fractionation stage can be purposively relatively enriched as well as relatively depleted, depending upon the molarity of the aqueous phase in the extraction stage (3).

A high molarity of the aqueous phase in (3) within the given molarity range leads to a relative depletion of higher nuclear components in the organic phase (D) and correspondingly to a relative enrichment in the aqueous phase (H).

A low molarity of the aqueous phase in (C) within the given molarity range leads to a relative enrichment of higher nuclear components in the organic phase (D). This surprising finding can be extended and stated more precisely to the effect that the relative enrichment and depletion also occurs in the higher nuclear homologues between one another. If, for example, in a technical mixture of diaminodiphenylmethane, in one fraction the trinuclear components are relatively enriched or depleted as compared with the dinuclear components, a relative enrichment or depletion of tetranuclear components as compared with trinuclear components, that is, an even greater relative enrichment or depletion, is found, likewise pentanuclear components as compared with tetranuclear components, and so on.

Out of this, and out of the separation of isomers proceeding simultaneously and invariably in the sense of a relative intensification of the "degree of ortho-substitution" in the organic phase (D), and out of the feasibility of repeating the separation according to the invention using individual product fractions, optionally with altered processing conditions, there arise numerous possibilities, starting from known and readily available polyamine mixtures, of obtaining by means of the process according to the invention polyamines and hence polyisocyanates which are less readily available or are completely new because they have hitherto been unavailable according to prior art. This applies in particular to products of the diamino- and diisocyanatodiphenyimethane series and most particularly to polyamine mixtures and polyisocyanate mixtures having an extremely high proportion of higher nuclear components.

The enrichment or depletion becomes more efficient as a rule with an increasing degree of protonation in the aqueous phase of the separator stage.

The process according to the invention proves moreover to be generally effective for other structurally similar polyamines as well. Thus, for example, the polyamine mixtures already mentioned, which are obtained by nitration of di- and polyarylmethanes and subsequent reduction, can also contain monoaminopolyarylmethane compounds or components, wherein one or more methylene groups have been converted by secondary reactions into keto groups and/or hydroxymethylene groups and thence into undesirable by-products.

Numerous incompletely rearranged intermediate compounds and by-products can appear during the condensation of arylamines with carbonyl compounds. Most of these compounds are as a rule subject, during the fractionation of the polyamine mixtures containing them, to an enrichment in one of the resulting fractions, so that the effect can be utilized for separation and fractionation.

Optionally products of this kind can be enriched or depleted in this manner, or can on their part be fractionated as purposively prepared polyamine mixtures such as, for example, polyaminobenzophenones or aminobenzylarylamine mixtures.

The organic phase (D) leaving the extraction stage (3) still contains inter alia small quantities of acid, in general and depending upon the processing conditions in the extraction stage (3), of between 0.01 and 0.5 wt. %, which are advantageously removed before the stream (D) is worked up by distillation.

In the simplest case this is carried out by neutralization using excess, dilute aqueous bases, for example, dilute sodium hydroxide solution. Preferably, however, the acid or the amine salts thereof are washed out of the organic phase using water, so that traces of acid possibly still remaining are removed by contact with dilute sodium hydroxide solution or by means of an ion exchanger.

The washings used are withdrawn from the aqueous acid circulation by insertion of a water evaporator and after passing through the washing stage(s) are again added thereto together with the acid at a place appropriate to the procedure.

The organic phase (D) or (D'), optionally after passing through the acid washing stage (7.0), is transferred to the at least two-stage distillation stage (7.1), (7.2).

In the first distillation stage (7.1) a distillate (E) is separated off which comprises the main quantity, preferably virtually the entire quantity, of the hydrophobic solution contained in (D) or D') together with a part of the auxiliary amine contained therein.

In the final distillation stage (7.2) the remaining auxiliary amine, optionally together with the residual quantity of hydrophobic solvent, is separated off as distillate (F) from the first partial product (G) obtained as distillation bottoms and collected in the tank (10) for receiving the product of the process.

The corresponding second product of the process is in the aqueous phase (H) leaving the extraction stage (3).

In an extraction stage (5) operating in multiple stages preferably at 80° to 110° C., the second partial product from the aqueous phase (H), optionally after addition of water to decrease the molarity and optionally after addition of auxiliary amine to decrease the degree of protonation, is extracted in exchange for auxiliary amine and in the course of this transferred into the organic phase (L).

The molarity of the aqueous phase used in (5) is preferably <2.5, while the degree of protonation of the aqueous phase used in (5) is preferably <60%.

The extracting agent (J) used is a mixture of hydrophobic solvent and auxiliary amine, which is formed substantially from the organic phase (R) leaving the subsequent extraction stage (6), optionally distillate (M) and as a rule a partial quantity of the stream (S).

The weight ratio of auxiliary amine to solvent in (J) is generally between 0.5:1 and 3:1, preferably between 1:1 and 2:1. The weight ratio of extracting agent (J) to aqueous phase is generally between 0.3:1 and 3:1, preferably between 0.7:1 and 2:1.

The organic phase (L) or (L') obtained in (5), optionally after passing through the washing stage (8.0) and/or optionally after removal of traces of acid using dilute sodium hydroxide solution, is led to the distillation stages (8.1) and (8.2).

The separation by distillation of the distillation residue (O), which is collected as second partial product-in the tank (11) for receiving the product of the process, is carried out in the distillation stage (8.1), (8.2).

The working-up stage (8) consists in general of an at least two-stage multiple-stage distillation (8.1) and (8.2). In stage (8.1) a hydrophobic solvent which, compared with the feed product (L) or (L'), is free from polyamine and greatly depleted of auxiliary amine is recovered as distillate (M).

The content of auxiliary amine in (M) is generally <30%, preferably <20%; optionally a hydrophobic solvent freed from auxiliary amine is recovered as distillate in (8.1).

The distillate (M), optionally also after addition of a partial quantity of (E) from the distillation stage (7.1), is used at least partly in the extraction stage (6) in the form of organic phase (P) for the countercurrent extraction of at least a partial quantity of the aqueous phase (K) obtained in the extraction stage (5), at least part of which phase (K) is led to the extraction stage (6) directly and/or indirectly via an interposed distillation stage (9).

In the extraction process proceeding in the extraction stage (6), auxiliary amine and optionally polyamine still present are removed from the aqueous phase, so that the resulting aqueous phase (Q) invariably has a higher degree of protonation than that of the aqueous phase (K) from the extraction stage (5).

The degree of protonation of (Q) is in general >50%, preferably >60%, and can be up to 100% when pure hydrophobic solvent is used a (P).

The reused aqueous phase (C) has a higher degree of protonation than that of the aqueous phase (K) leaving the extraction stage (5). Degrees of protonation higher than those of (K) but less than 100% can be achieved by passing either the entire aqueous phase through the extraction stage (6), or only an appropriate partial quantity which, optionally having a degree of protonation of 100%, through mixture with the residue yields the degree of protonation of (C) increased as compared with (K).

A degree of protonation of virtually 100% in the aqueous phase (C) can only be achieved when the entire aqueous phase passes at least once through the extraction stage (6) and in the course of this is extracted using virtually pure hydrophobic solvent.

Since the aqueous phase (C) according to the invention has a higher degree of protonation than the preferred degree of protonation in the aqueous inlet phase to the extraction stage (5), it may be necessary and advantageous, by addition of auxiliary amine and/or polyamine at a suitable place, to establish such a preferred degree of protonation in the aqueous inlet phase to the extraction stage (5).

Suitable places for the introduction of amine are the aqueous phase immediately prior to entry into the extraction stage (5) using auxiliary amine, or at a place positioned in front, preferably prior to entry of the aqueous phase into the extraction stage (3), for example, by direct addition or via an extraction stage (2) serially connected in front.

The molarity is another important variable of the returned and reused aqueous phase (C). According to the invention the molarity of (C) can be varied within a wide range depending on the respective problem of separation.

In principle the aqueous phase (H) obtained in the extraction stage (3) can be passed to the extraction stage (5) directly or optionally via an intermediate stage (4). However, since the above molarity range of the extraction stage (3), definitely preferred for particular problems of separation, is above the preferred molarity range of the extraction stage (5), a preferred embodiment of the process according to the invention is to segregate the molarities in the different extraction stages by withdrawing water by means of distillation from the self-contained system of the aqueous phase optionally at a suitable place and reintroducing it at another suitable place.

By means of a water distillation stage (9), water is withdrawn from the aqueous phase containing the acid, or from a partial stream of the aqueous phase, preferably after leaving the extraction stage (5) and prior to reuse at the beginning of the process. This withdrawn water is reintroduced prior to entry of the aqueous phase into the extraction stage (5) altogether (Y) or in partial quantities.

Whether the withdrawal of water in (9) takes place prior to or after passage through the extraction stage (6) is unimportant in carrying out the process according to the invention.

The water (X) withdrawn in (9) can be utilized simultaneously for the operation of the washing stages (7.0) and/or (8.0). The mass of water (X) can also be withdrawn chiefly or exclusively for the operation of the washing stages (7.0) and/or (8.0). By means of this first variant of the process according to the invention, considerable separation efficiency in the fractionation of polyamine mixtures can be achieved and numerous problems in separation can be satisfactorily solved.

Particularly in the case of the first polyamine fraction (G) the relative enrichment of the components preferably contained in this fraction can be purposively varied and maximized.

The proportion of these components remaining in the second polyamine fraction (O) cannot, however, be minimized in the same way by this first variant, but can be relatively enriched variably only up to a content the lower limit whereof is dependent on the distribution equilibrium, which is characteristic for the respective processing conditions, of the polyamine components of (A) between the organic phase (B) on entry into the extractor (3) and the aqueous phase (H) on leaving the extractor (3).

Through the admixture of proportions of the second polyamine fraction (O), preferably as a partial stream of (L), to the starting arylamine (A), the content of components of (G) in the latter can be relatively lowered and thereby, through the distribution equilibrium, the lower limit in these components attainable by the first variant can be shifted into the second partial product (O). The only slight improvement in the separation efficiency achieved thereby may be adequate for certain applications, but is as a rule at the cost of the throughput of (A).

More advantageous, and preferred as an embodiment, is a second variant of the process according to the invention whereby, in the second polyamine fraction (O) as well, the relative enrichment of the components preferably contained in this fraction can be purposively varied largely independently of the first product fraction, by extracting the aqueous phase (H) obtained in the extraction stage (3), or at least a partial quantity of the same, using an organic phase (T) in an interposed extraction stage (4) operating according to the countercurrent principle.

The organic phase (T) generally consists, in addition to hydrophobic solvent, of auxiliary amine and/or polyamine, the latter preferably having the composition of the second partial product (O) of the process.

When an organic phase (T) is used without polyamine, the result is that in the aqueous phase (V) leaving the extraction stage (4) a polyamine fraction is formed wherein the relative enrichment of the components preferably contained in this phase can be purposively increased and maximized over and above the enrichment obtained in the aqueous phase (H), at the cost of the polyamine concentration in the aqueous phase (V).

The presence of polyamine as component of the organic phase (T) causes the phases (U) and (V) leaving the processing stage (4) to have a polyamine concentration which is higher, and therefore energetically more favorable for carrying out the process according to the invention, than when an organic phase (T) is used without polyamine.

Through the preferred use of a polyamine having the composition of the second partial product (O) as component of the organic phase (T), the relative enrichment of the polyamine components preferably contained in the aqueous phase (V) leaving the separator stage (4) and hence the second polyamine fraction (O) can also be varied and maximized at a higher and hence advantageous concentration level, owing to establishment of equilibrium together with self-reinforcement of the separator effect.

In the simplest and most general case, the organic phase (T) is formed from at least one partial stream from stream (E) and optionally further auxiliary amine from stream (S). Preferably stream (T) is formed optionally from a partial quantity of (E), optionally from a partial quantity of (S) and a partial quantity of the stream (L) containing the polyamine mixture (O).

The supply of hydrophobic solvent and auxiliary amine from other sources can optionally be wholly dispensed with, so that the organic phase (T) consists exclusively of a partial quantity of (L). This embodiment of the process according to the invention is particularly advantageous with regard to separation efficiency and energy balance and is therefore particularly preferred when it can be applied.

The molarity of the aqueous phase used in the interposed extraction stage (4) is generally of the same value as that of the aqueous phase (H) leaving the extraction stage (3). It is however possible, by the addition to the aqueous phase of water and optionally of auxiliary amine, to alter both the molarity and the degree of protonation in order to improve the separation efficiency according to the process.

In principle it is also possible to increase the molarity of the aqueous phase used in (4) by withdrawing water by means of distillation.

The organic phase (U) obtained in stage (4) is added to the organic phase (B) used in extraction stage (3).

The aqueous phase (V) obtained in stage (4), optionally together with the residue from (H), is added to the extraction stage (5).

The quantity of hydrophobic solvent which, in order optionally to form the extracting agent (T), is withdrawn from the solvent circulation of the second product (O) of the process by diverting a partial stream from (L), is quantitatively compensated for preferably by addition of a partial quantity of (E) during the formation of the organic phases (P) and/or (J).

By means of the second variant of the process according to the invention, the relative enrichment can be purposively varied and maximized in both of the resulting polyamine fractions. In addition to this qualitatively high versatility and efficiency, the second procedural variant also offers an energetically favorable embodiment, at least for the second polyamine fraction (O).

However, the expense associated with the recovery of the first polyamine fraction (G) increases relatively more sharply, the smaller the quantitative proportion of (G) is, referred to the polyamine mixture (A) used, because the remaining content of polyamine (G) in the organic phase (D) to be worked up by distillation becomes correspondingly smaller. This effect is brought to bear particularly when the components in starting mixture (A) separated off together with (G) are contained only in a low concentration and/or are relatively highly enriched in the fraction (G), for example, in the separation according to the invention of polyamine mixtures of the diphenylmethane series.

An introduction of pad of starting polyamine (A) into the separator stage (3) via the aqueous phase supplied produces as a rule an increase in the polyamine concentration in (D) and therewith a release of energy. In the performance of the process according to the invention, however, owing to the establishment of equilibrium between the polyamine in the aqueous phase introduced and the polyamine in the organic phase (D), this release is associated with a deterioration in the qualitative results of separation in the first partial product (G), so that use is made of this eventuality only to a minor extent or in cases where the requirements for the results of separation are correspondingly low.

The third variant of the process according to the invention is an improved performance in this respect. Proceeding from the first variant, the latter is extended to the effect that the organic phase (D) leaving the processing stage (3) and containing the first partial product (G) in a diminished concentration as compared with the concentration of (A) in (B) is divided into a stream (D'), which is passed further on to the working-up stage (7) for the purpose of recovering the polyamine fraction (G), and a stream (D").

The stream (D") is extracted in countercurrent in an extraction stage (2) positioned in front, using at least a partial quantity, preferably the entire quantity of the aqueous phase (C) available for reuse.

Here the stream (D") passed to the extractor (2) is so calculated that during the interaction with stream (C) an as extensive as possible, preferably virtually quantitative, transition of the polyamine contained in the organic phase (D") into the aqueous phase leaving the extractor (2) takes place, so that an organic phase (Z) is obtained which is freed as far as possible from polyamine.

An increased degree of protonation in the aqueous phase used in stage (2), resulting from the processing stage (6) of the process according to the invention, likewise an increased molarity in the aqueous phase used in stage (2), resulting from the processing stage (9) of the process according to the invention, promotes and facilitates the transition of polyamine from the organic phase (D") into the aqueous phase.

The residual content of polyamine in the organic phase (Z) leaving the processing stage (2) is generally <5 wt. %, preferably <1 wt. %.

Incidentally the highest content of amine and in particular the content of polyamine permissible in (Z) is determined by the qualitative requirements for the products of the process resulting from the respective problem of separation, that is, the quality of the separation, in the case of variant 3 in particular, the requirements for the partial product (O) of the process. The maintenance of the polyamine content appropriate for the quality of (O) is controlled within the limits of the technical conditions by utilizing the available potential of aqueous phase (C) via the measurement of the partial stream (D").

Quantitatively it is useful to the process and in particular to the processing stage (2) positioned in front, that the proportion of (D") to (D') should tend particularly towards higher values, that is, that (D") should be quantitatively greater, when the proportion of the polyamine fractions (G) to (O) becomes smaller, because (O) becomes greater at the expense of (G). With an increasing proportion of the second polyamine fraction (O), the aqueous phase (C) circulated and hence available in (2) for the extraction of (D") is increased.

The organic phase (Z) depleted of amine, virtually freed in particular from polyamine and leaving the processing stage (2) is added to the organic phase (B) and passed together with the latter to the processing stage (3) as solvent for the starting polyamine (A).

The aqueous phase leaving the processing stage (2) contains, in addition to the aqueous acid used, polyamine the composition whereof largely corresponds to that of the polyamine separated in (D) and isolated as fraction (G), and optionally auxiliary amine.

In the simplest case the aqueous phase leaving the processing stage (2) is passed directly to the processing stage (3) as stream (C); optionally further aqueous phase and/or water and/or auxiliary amine are added beforehand.

The addition of a limited quantity of starting polyamine (A) to the aqueous phase is also possible according to variant 3, without loss of qualitative separation efficiency (relative enrichment) as compared with variant 1, but with improved quantitative efficiency (greater economy).

In a further, fourth variant the processing stage (2) positioned in front, together with its ensuing advantages, is combined with the embodiment of the process according to the invention described as variant 2, which is thereby improved with regard to the first partial product in a manner similar to that described for variant 3. An additional facilitation and simplification in carrying out the processing stage (2) has proved to be that the requirements for the polyamine content remaining in the organic phase (Z) obtained in (2) are less stringent, since the adverse effects of an increased polyamine content in (Z) on the quality of the second partial product (O) of the process can be compensated for by the extraction stage (4) serially connected behind.

The content of polyamine in the organic phase (Z) leaving the processing stage (2) is therefore generally <5 wt. %, preferably <3 wt. %.

The invention is further illustrated but is not intended to be limited by the following examples in which all parts and percentages are by weight unless otherwise specified.

EXAMPLE

The starting mixture of polyamines (A) (2.600 kg/h) is mixed with the stream (B) (7.835 kg/h) consisting substantially of polyamine mixture, aniline and xylene.

Stream (B) is formed substantially from stream (U) (4.255 kg/h) and stream (Z) (3.580 kg/h).

The resulting organic phase (streams A+B) has the following average composition:

| Stream (A) + (B) (10.435 kg/h) | 43.4% polyarylamine 7.9% aniline 48.7% xylene |
|---|---| and is passed through a multiple-stage extractor (3) at 90° C. to 95° C. counter to the stream (C), which has the following average composition:

| Stream (C) (28.650 kg/h) | 4.4% polyarylamine 11.9% aniline 3.3% hydrogen chloride 80.4% water. |
|---|---|

The organic phase (D) leaving the extractor (3) has the following average composition:

| Stream (D) (10.650 kg/h) | 21.5% polyarylamine 30.8% aniline 47.7% xylene. |
|---|---|

Stream (D) is divided into partial stream (D"), which is led to the extraction stage (2) and into the stream (D') (4.870 kg/h). Stream (D') is washed with water (about 0.5–1.0 kg/h) in the extractor (7.0). The resulting washings from (7.0) [similarly from (8.0)] are collected in stream (Y).

As a precaution stream (D') is washed with dilute sodium hydroxide solution. The aqueous phase is removed as waste water.

In a first distillation stage (7.1) a first distillate fraction (E) is separated off from the stream (D') previously washed and freed from acid residues. The resulting distillation residue is separated in a second distillation stage (7.2) into a second distillate fraction (F), a partial quantity of (S), and a distillation residue (G).

The distillation residue from distillation stage (7.2) consists of a first polyamine fraction (G) at 1.045 kg/h and is collected in tank (10).

The aqueous phase (H) leaving the extractor (3) has the following average composition

| Stream (H) (28.435 kg/h) | 12.3% polyarylamine 3.4% aniline 3.3% hydrogen chloride 81.0% water |
|---|---| and is passed through another multiple-stage extractor (4) at 90° C. to 95° C. counter to an organic phase (T) [Stream (T) 5.150 kg/h], which is a partial quantity of the organic phase (L).

The organic phase (U) [Stream (U) 4.255 kg/h] obtained in processing stage (4) enters stream (B) and is passed to the processing stage (3).

The aqueous phase (V) [Stream (V) 29.330 kg/h] obtained in the extractor (4) is passed through another multiple-stage extractor (5) at 90° C. to 95° C. counter to the stream (J):

| Stream (J) (13.070 kg/h) | <0.1% polyarylamine 50.2% aniline 49.7% xylene. |
|---|---|

The organic phase (L) leaving the extractor (5) is obtained having the following average composition

| Stream (L) (14.400 kg/h) | 16.8% polyarylamine 38.1% aniline 45.1% xylene |
|---|---| and is divided into the partial stream which is passed as stream (T) to the extraction stage (4), and the stream (L').

Stream (L') (9.250 kg/h) is washed with water (about 1.0–1.5 kg/h) in an extrador (8.0). The resulting washings are collected in the stream (Y).

As a precaution stream (L') is washed with dilute sodium hydroxide solution. The aqueous phase is removed as waste water.

The stream (L'), which has been washed and freed from acid residues, is then separated in a first distillation stage (8.1) into a first distillate fraction (M) [Stream (M) 4.200 kg/h], which consists virtually of xylene having an aniline content of at most 1% and into distillation bottoms, which are separated in a second distillation stage into a second distillate fraction (N) [Stream (N) 3.495 kg/h], a partial quantity of (S) consisting visually of aniline, and into a distillation residue (O) [Stream (O) 1.555 kg/h] consisting of polyamine.

The polyamine fraction (O) is collected in tank (11) as the second partial product.

The distillate fraction (E) and stream (S) are passed to the extraction stage (5) and together with stream (R) form the organic inlet phase (J).

The aqueous phase (K) leaving the extractor (5) has the following average composition

| Stream (K) (28.000 kg/h) | 0.2% polyarylamine 14.2% aniline 3.3% hydrogen chloride 82.3% water |
|---|---| and is passed through another multiple-stage extractor (6) at 90° C. to 95° C. counter to an organic phase (P); in the present case (P) is identical in quantity and composition with the first distillate fraction (M) from the distillation stage (8.1).

The organic phase resulting from this process is the stream (R),

| Stream (R) (5.750 kg/h) | <0.2% polyarylamine 27.4% aniline 72.6% xylene. |
|---|---|

The aqueous phase (Q) obtained in (6) has the following average composition:

| Stream (Q) (26.450 kg/h) | 0.2% polyarylamine 9.2% aniline 3.5% hydrogen chloride 87.1% water. |
|---|---|

In a subsequent distillation stage (9), water is withdrawn from the aqueous phase (Q) by distillation in the form of the stream (X) (about 1.5–2.5 kg/h).

The water distilled off is used in partial streams for washing the organic phases in the washing stages (7.0) and (8.0). The resulting washings are combined in the stream (Y).

The concentrated aqueous phase (W) obtained in (9) is passed through extraction stage (2) positioned in front, at 90° C. to 95° C., counter to the organic partial stream (D"). During this multiple-stage process an organic phase (Z) is obtained having the following composition:

| Stream (Z) (3.580 kg/h) | <1% polyarylamine 21.8% aniline 77.1% xylene |
|---|---| which is employed to form part of the stream (B).

The aqueous phase obtained in the extraction stage (2) is combined with stream (Y) and passed as aqueous phase (C) to the extractions phases (3).

Organic phases and aqueous phases are passed counter to one another through the extraction stages (2) to (6). This results on the one hand in low contents of hydrogen chloride and water in the organic phases and on the other hand in low contents of xylene in the aqueous phases. These are not taken into account in the balancing and characterization of the streams.

The quantities of acid and water withdrawn from the system during the wash with sodium hydroxide solution via the precautionary neutralization stages are replaced by addition from outside.

| Polyarylamine GC: | A [wt. %] | G [wt. %] | O [wt. %] |
|---|---|---|---|
| 2,2'-diaminodiphenylmethane | <0.10 | <0.10 | — |
| 2,4'-diaminodiphenylmethane | 0.72 | 1.80 | <0.10 |
| 4,4'-diaminodiphenylmethane | 66.00 | 17.50 | 98.60 |
| N-methyl-4,4'-diaminodiphenyl-methane | 0.10 | 0.20 | — |
| Σ-diaminodiphenylmethane | 66.90 | 19.50 | 98.60 |
| Σ-polynuclear polyamines | 33.10 | 80.50 | 1.30 |
| Quantitative distribution | 100% | 40.2% | 59.8% |

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for the fractionation and purification of aromatic polyamine mixtures comprising:
    a) mixing the polyamine starting mixture in a first extraction stage with a two-phase system comprising
        (i) a hydrophobic solvent phase which consists essentially of hydrophobic solvent and optionally an aromatic auxiliary amine which is substantially insoluble in water and exhibits at normal pressure a boiling point which is at least 20° C. below the boiling point of the lowest-boiling component of the starting mixture and at least 20° C. above the boiling point of the solvent, and optionally polyamine, and
        (ii) an aqueous phase consisting essentially of water, a strong acid and auxiliary amine present at least in part in the salt form, and optionally polyamines present at least in part in the salt form,
        with said first extraction stage operating on the countercurrent principle, and wherein said polyamine starting mixture is introduced into said first extraction stage with said hydrophobic solvent phase, with a first aqueous phase and a first organic phase exiting said first extraction stage,
    b) distilling said first organic phase in a first multi-stage distillation into
        i) a first fraction consisting essentially of hydrophobic solvent and optionally auxiliary amine,
        ii) a second fraction consisting essentially of auxiliary amine and optionally hydrophobic solvent, and
        iii) a distillation residue consisting essentially of a first polyamine fraction,
    c) extracting said first aqueous phase in a second extraction stage with a solvent phase consisting essentially of hydrophobic solvent and auxiliary amine, said second extraction stage operating on the countercurrent principle, with i) a second aqueous phase, said second aqueous phase being reduced in polyamine content and ii) a second organic phase exiting said second extraction stage,
    d) separating at least a portion of said second organic phase in a second multistage distillation into
        i) a first fraction consisting essentially of hydrophobic solvent and optionally proportions of auxiliary amine,
        ii) a second fraction consisting essentially of auxiliary amine and optionally proportions of hydrophobic solvent, and
        iii) a distillation residue consisting essentially of a second polyamine fraction, e) extracting at least a portion of said second aqueous phase in a third extraction stage with an organic phase consisting essentially of hydrophobic solvent and optionally auxiliary amine, said third extraction stage operating on the countercurrent principle, with i) a third aqueous phase, said third aqueous phase being reduced in amine content and ii) a third organic phase exiting said third extraction stage, f) recycling said third aqueous phase as at least a portion of said aqueous phase, and g) recycling said third organic phase to said second extraction stage as at least a portion of said solvent phase.

2. A process for the fractionation and purification of mixtures of aromatic polyamines which is characterized in that a) the starting polyamine mixture (A) is distributed, by means of an extraction stage (3) operating according to the countercurrent principle, in a two-phase system, consisting of (i) a hydrophobic solvent phase (B), which consists substantially of hydrophobic solvent, and optionally of an aromatic auxiliary amine, which amine is virtually insoluble in water and at normal pressure has a boiling point at least 20° C. below the boiling point of the lowest boiling component of the starting mixture and at least 20° C. above the boiling point of the solvent, and optionally of polyamines, and (ii) an aqueous phase (C), consisting substantially of water, a strong acid and auxiliary amine present at least partly in the form of salt, and optionally polyamines present at least partly in the form of salt, with thorough mixing of the phases, by introducing the starting polyamine mixture into the extraction stage (3) preferably via the organic phase (B), by at least partly separating the organic phase (D) leaving this extraction stage, optionally after passing through a washing stage (7.0), in a multiple-stage distillation (7.1), (7.2) into a first fraction (E) which is reused in the extraction stage (3) and consists substantially of hydrophobic solvent and optionally auxiliary amine, into a second fraction (F), consisting substantially of auxiliary amine and optionally of hydrophobic solvent, and a distillation residue (G), consisting substantially of a first polyamine fraction, and by passing the aqueous phase (H) leaving the extraction stage (3), b) optionally at least partly via an interposed extraction stage (4), c) into an extraction stage (5), wherein the aqueous phase is extracted according to the principle of countercurrent extraction, using a solvent phase (J) consisting of hydrophobic solvent and auxiliary amine, and the aqueous phase (K) depleted of polyamine results, and d) by at least partly separating the organic phase (L) obtained in the extraction stage (5), optionally after passing through a washing stage (8.0), in a multiple-stage distillation (8.1), (8.2) into a first fraction (M), consisting substantially of hydrophobic solvent and optionally small proportions of auxiliary amine, and into a second fraction (N) consisting substantially of auxiliary amine and optionally small proportions of hydrophobic solvent and a distillation residue (O), consisting substantially of a second polyamine fraction, and e) by passing at least partly the aqueous phase (K) obtained in the extraction stage (5), f) optionally via an interposed distillation stage (9)

g) into an extraction stage (6) and by extracting it in countercurrent using an organic phase (P), consisting substantially of hydrophobic solvent and optionally at most sufficient auxiliary amine to obtain in (6) an aqueous phase (Q) depleted of arylamine as compared with the aqueous phase (K) introduced, which phase (Q), h) optionally at least partly via an interposed distillation stage (9)

i) is combined with the residue of (Q) optionally present and is reused as stream (C), by passing stream (C)

j) optionally at least partly via an extraction stage (2) serially connected in front k) optionally after addition of auxiliary amine and/or water, to the extraction stage (3) and l) by passing the organic phase (R) obtained in the extraction stage (6), optionally after addition of another organic phase, consisting substantially of auxiliary amine and diverted from stream (S), as extracting agent (J) to the extraction stage (5).

3. The process of claim 2, wherein b) the aqueous phase (H) obtained in the extraction stage (3) is extracted at least partly in an extraction stage (4) serially connected behind and operating according to the countercurrent principle, using as extracting agent an organic phase (T) which consists, in addition to hydrophobic solvent, of auxiliary amine and optionally of polyamine, the latter preferably having the composition of the second partial product (O) and preferably introduced as a partial quantity of the stream (L); the resulting organic phase (U) in the processing stage (4) is passed to the stream (B) and therewith to the extraction stage (3) and the resulting aqueous phase (V) is passed to the extraction stage (5).

4. The process of claim 2, wherein j) a partial quantity (D") of the organic phase (D) leaving the extraction stage (3) is separated off and is extracted in a preferably multiple-stage extraction stage (2) positioned in front, using preferably the entire stream (C) in countercurrent, optionally with the addition of auxiliary amine, and the partial stream (D") is calculated so that as extensive a transition as possible of the polyamine contained in (D") into the aqueous phase leaving the extraction stage (2) takes place, the said aqueous phase, optionally after addition of water from stream (Y) and/or auxiliary amine and/or further aqueous phase from stream (C), is passed to the extraction stage (3), the organic phase (Z) obtained in (2) and consisting substantially of hydrophobic solvent and optionally auxiliary amine is likewise passed to the extraction stage (3) and as a constituent of the organic phase (B) is used as solvent for the starting polyamine (A).

5. The process of claim 2, wherein the reused stream (C) exhibits a higher degree of protonation than that of the aqueous phase (K) leaving the penultimate extraction stage (5), optionally by up to 100%.

6. The process of claim 2, wherein f) at least partly the aqueous phase (K) leaving the extraction stage (5) prior to reuse thereof and/or at least partly the aqueous phase (Q) leaving the extraction stage (6) prior to reuse thereof are freed, by means of distillation (9), from a portion (X) of the water contained therein, the latter is used optionally for washing (7.0) the portion of the organic phase (D) leaving the extraction stage (3) and led away for working up by distillation (7.1), (7.2) and/or for washing (8.0) the portion of the organic phase (L) leaving the extraction stage (5) and led away for working up by distillation (8.1), (8.2), in order to remove traces of acid, the water (Y) obtained here is returned to the aqueous phase at a suitable place, the resulting concentrated aqueous phase is combined with the optionally remaining residues of (K) and (Q) and returned for reuse as stream (C).

7. The process of claim 2, wherein aniline is used as auxiliary amine.

8. The process of claim 2, wherein the polyamine mixture used is a polyamine mixture of the diphenylmethane series obtained during the acid-catalyzed aniline/formaldehyde condensation.

9. In a process for the preparation of a polyisocyanate by phosgenating an aromatic polyamine, the improvement wherein the aromatic polyamine is prepared by the process of claim 1.

10. In a process for preparing a cycloaliphatic polyamine by hydrogenating an aromatic polyamine, the improvement wherein the aromatic polyamine is prepared by the process of claim 1.

* * * * *